(12) United States Patent
Prus et al.

(10) Patent No.: US 11,986,682 B2
(45) Date of Patent: May 21, 2024

(54) ULTRASOUND AUTOFOCUSING USING REFLECTIONS

(71) Applicants: Oleg Prus, Haifa (IL); Yoav Levy, Hinanit (IL)

(72) Inventors: Oleg Prus, Haifa (IL); Yoav Levy, Hinanit (IL)

(73) Assignee: Insightec Ltd., Tirat Carmel (IL)

( * ) Notice: Subject to any disclaimer, the term of this patent is extended or adjusted under 35 U.S.C. 154(b) by 481 days.

(21) Appl. No.: 16/314,985

(22) PCT Filed: Aug. 3, 2017

(86) PCT No.: PCT/IB2017/000990
§ 371 (c)(1),
(2) Date: Jan. 3, 2019

(87) PCT Pub. No.: WO2018/020315
PCT Pub. Date: Feb. 1, 2018

(65) Prior Publication Data
US 2019/0308038 A1 Oct. 10, 2019

Related U.S. Application Data

(60) Provisional application No. 62/366,200, filed on Jul. 25, 2016.

(51) Int. Cl.
*A61B 8/00* (2006.01)
*A61B 8/08* (2006.01)
(Continued)

(52) U.S. Cl.
CPC .............. *A61N 7/02* (2013.01); *A61B 8/0808* (2013.01); *A61B 8/4488* (2013.01);
(Continued)

(58) Field of Classification Search
CPC .............. A61N 7/02; A61N 2007/0039; A61N 2007/0052; A61N 2007/0078;
(Continued)

(56) References Cited

U.S. PATENT DOCUMENTS 5,092,336 A 3/1992 Fink
5,380,411 A 1/1995 Schlief
(Continued)

FOREIGN PATENT DOCUMENTS

CN 102657612 9/2012
GB 2515134 A 12/2014
(Continued)

OTHER PUBLICATIONS

International Search Report and Written Opinion of the International Searching Authority for International Application No. PCT/IB2017/00990, dated Nov. 16, 2017, 2018, 20 pages.
(Continued)

*Primary Examiner* — Christopher L Cook
(74) *Attorney, Agent, or Firm* — Morgan, Lewis & Bockius LLP

(57) ABSTRACT

Various approaches of focusing an ultrasound transducer having multiple transducer elements to a target region include generating at least one acoustic reflector in the target region; transmitting ultrasound waves to the acoustic reflector; measuring reflections off the acoustic reflector; and based at least in part on the measured reflections, adjusting the parameter value associated with the transducer element(s).

15 Claims, 5 Drawing Sheets

(51) Int. Cl.
*A61N 7/02* (2006.01)
*A61B 17/00* (2006.01)
*A61B 17/22* (2006.01)
*A61B 90/00* (2016.01)
*A61N 7/00* (2006.01)

(52) U.S. Cl.
CPC ............ *A61B 8/4494* (2013.01); *A61B 8/481* (2013.01); *A61B 8/585* (2013.01); *A61B 2017/00106* (2013.01); *A61B 2017/22008* (2013.01); *A61B 2090/378* (2016.02); *A61N 2007/0039* (2013.01); *A61N 2007/0052* (2013.01); *A61N 2007/0078* (2013.01); *A61N 2007/0095* (2013.01)

(58) Field of Classification Search
CPC .............. A61N 2007/0095; A61B 8/00; A61B 2017/00106; A61B 2007/0039; A61B 2017/22008; A61B 2090/378; A61B 8/0808; A61B 8/4488; A61B 8/4494; A61B 8/481; A61B 8/585
See application file for complete search history.

(56) References Cited

U.S. PATENT DOCUMENTS

| | | | |
|---|---|---|---|
| 6,309,355 B1 | 10/2001 | Cain et al. | |
| 6,558,328 B2 | 5/2003 | Chiao et al. | |
| 6,591,129 B1 | 7/2003 | Ben-Haim et al. | |
| 7,771,359 B2* | 8/2010 | Adam | G10K 11/32 600/458 |
| 7,905,836 B2 | 3/2011 | Dan | |
| 8,617,073 B2* | 12/2013 | Prus | A61B 8/14 600/437 |
| 10,589,129 B2* | 3/2020 | Vortman | A61N 7/022 |
| 2003/0187371 A1 | 10/2003 | Vortman et al. | |
| 2006/0206028 A1 | 9/2006 | Yu | |
| 2010/0030076 A1* | 2/2010 | Vortman | A61N 7/02 600/439 |
| 2010/0241036 A1 | 9/2010 | Vortman et al. | |
| 2011/0094288 A1* | 4/2011 | Medan | G10K 11/346 73/1.82 |
| 2013/0006106 A1* | 1/2013 | O'Reilly | A61B 8/0808 600/431 |
| 2013/0053678 A1 | 2/2013 | Fink | |
| 2015/0335919 A1 | 11/2015 | Behar et al. | |

FOREIGN PATENT DOCUMENTS

| | | |
|---|---|---|
| WO | 2006030534 | 3/2006 |
| WO | 2012019172 | 2/2012 |
| WO | 2014008594 | 1/2014 |
| WO | 2014138050 A1 | 9/2014 |

OTHER PUBLICATIONS

Haworth, et al., Towards Aberration Correction of Transcranial Ultrasound Using Acoustic Droplet Vaporization, 2008, Ultrasound in Med. & Biol., vol. 34, No. 3, pp. 435-445.

Insightec, Ltd., Third Office Action, CN201780044193.2, Jul. 28, 2021, 21 pgs.

* cited by examiner

ULTRASOUND AUTOFOCUSING USING REFLECTIONS

RELATED APPLICATION

Cross-Reference to Related Application

This application is a U.S. National Phase Application of PCT/IB2017/000990, filed Jul. 19, 2017, which claims the benefit of and priority to U.S. Provisional Patent Application No. 62/366,200, filed Jul. 25, 2016. The foregoing applications are incorporated herein by reference in their entireties.

FIELD OF THE INVENTION

The present invention relates, generally, to systems and methods for ultrasound autofocusing and, more particularly, to autofocusing using ultrasound reflections.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

The noninvasive nature of ultrasound surgery is particularly appealing for the treatment of brain tumors. However, the human skull has been a barrier to the clinical realization of ultrasound therapy. Impediments to transcranial ultrasound procedures include strong attenuation and the distortions caused by irregularities in the skull's shape, density, and sound speed, which contribute toward destroying the focus and/or decreasing the ability to spatially register received diagnostic information.

To overcome difficulties associated with the human skull, one conventional approach measures phase shifts resulting from travel of an ultrasound beam through the skull and subsequently adjusts ultrasound parameters to account for the aberrations caused at least in part by the skull. For example, a minimally invasive approach uses receiving probes designed for catheter insertion into the brain to measure the amplitude and phase distortion caused by the skull. Catheter insertions, however, still require surgery, which can be painful and can create a risk of infection.

An alternative, completely noninvasive approach uses X-ray computed tomography (CT) images, rather than receiving probes, to predict the wave distortion caused by the skull. In practice, however, computations of the relative phases alone may be too imprecise to enable high-quality focusing. For example, when ultrasound is focused into the brain to treat a tumor, the skull in the acoustic path may cause aberrations that are not readily ascertainable. In such situations, treatment is typically preceded by a focusing procedure in which an ultrasound focus is generated at or near the target, the quality of the focus is measured (using, e.g., thermal imaging or acoustic radiation force imaging (ARFI)), and experimental feedback is used to adjust the phases of the transducer elements to achieve sufficient focus quality.

The preceding focusing procedure, however, may take a substantial amount of time, which may render it impracticable or, at the least, inconvenient for a patient. In addition, ultrasound energy is inevitably deposited into the tissue surrounding the target during the procedure, thereby potentially damaging healthy tissue. While the effect of pretherapeutic sonications may be minimized by employing an imaging technique that requires only low acoustic intensity (e.g., ARFI), it is generally desirable to limit the number of sonications prior to treatment.

Accordingly, there is a need for more efficient and reliable ways of focusing ultrasound beams and creating a high-quality ultrasound focus.

SUMMARY

The present invention provides systems and methods for automatically focusing ultrasound beams at a target region when traversing tissue (such as a human skull) having an irregular structure, shape, density, and/or thickness using transient cavitation microbubbles. In various embodiments, each ultrasound transducer element is first energized to transmit waves having a phase shift and a power level sufficient to create a small cloud of transient microbubbles in the focus zone that is substantially close to the target region; the power levels and/or relative phases of the transducer elements used to create these microbubbles may be initially estimated based on a physical model including the geometries of the transducer elements, their locations and orientations relative to the target, and/or relevant material properties (e.g., the energy absorption of the tissue or the speed of sound at the employed frequency) along the beam path. Alternatively or additionally, the power levels and/or relative phases may be estimated based on the transmitted and/or reflected ultrasound measured either prior to treatment or during treatment (e.g., during treatment setup). In any case, perfect focus is unnecessary for generating the transient microbubble cloud since this cloud is itself used to establish the ultrasound focus for treatment purposes. So long as the initially estimated power levels and/or relative phases are sufficient to generate cavitation microbubbles at the target region, accounting perfectly for acoustic aberrations caused by inhomogeneous intervening tissue may be unnecessary at this stage.

Because the microbubbles encapsulate gas, the bubble surfaces may collectively form an ultrasound reflector. Ultrasound signals reflected from the bubbles may be therefore be utilized to establish a focus at the target region. Accordingly, after formation of the microbubbles, the transducer elements may be energized to direct ultrasound beams thereto, and ultrasound reflections from the bubbles may be analyzed. Based on the amplitudes and/or phases associated with the reflected ultrasound, the transducer parameters (e.g., phase shifts and/or amplitudes) may be adjusted in order to optimize the focus at the target region. These adjustments may be repeated until the detected reflection signals are consistent with an optimal focus. For example, if the amplitudes of the reflected signals are monitored during the process, optimal beam focusing may occur when the reflected amplitude reaches a maximum. Similarly, if phase information is extracted, optimal beam focusing may occur when the difference between reflected and transmitted phases reaches a minimum. Accordingly, through iterative cycles of measurement and adjustment as ultrasound is reflected from the microbubbles, a high-quality ultrasound focus may be reliably generated at the target region.

In one implementation, the ultrasound transducer is coupled to a controller including all necessary hardware components and/or software modules to automatically analyze the reflected signals received by the transducer and/or other detector(s), determine the phase/amplitude adjustments, and thereby automatically focus the ultrasound beams at the target region with satisfactory focusing properties. Alternatively, analysis of the reflected signals and/or adjustments of the transducer parameters may be performed manually by a user to focus ultrasound beams at the target region. The current invention thus allows the ultrasound beams to focus at the target region automatically or manually when traversing inhomogeneous tissue without the need to establish and rely on a physical model that predicts and accounts for aberrations resulting from the inhomogeneous tissue.

Accordingly, in one aspect, the invention pertains to a method of focusing an ultrasound transducer having multiple transducer elements on a target region. In various embodiments, the method includes (a) generating one or more acoustic reflectors in the target region; (b) transmitting the first ultrasound waves to the target region; (c) measuring reflections of the first ultrasound waves off the acoustic reflector; and (d) based at least in part on the measured reflections, adjusting a parameter value associated with one or more transducer elements so as to improve an ultrasound focus at the target region. The parameter value may include a frequency, a phase, or an amplitude of a signal driving the transducer element(s) for generating the first ultrasound waves. In one implementation, the parameter value is initially estimated based at least in part on a measurement of transmitted or reflected ultrasound waves. In addition, the method may further include introducing an ultrasound contrast agent into the target region.

The acoustic reflector may be generated by the first ultrasound waves and/or the second ultrasound waves that are transmitted to the target region prior to the first ultrasound waves. In one implementation, the second ultrasound waves have a value of a constitutive parameter different from that of the first ultrasound waves. The constitutive parameter may be, for example, an intensity level and/or a frequency associated with the ultrasound waves. In addition, the first ultrasound waves and/or the second ultrasound waves may be transmitted based at least in part on a physical model.

In various embodiments, the method further includes dividing the ultrasound transducer into multiple sub-regions, each sub-region having multiple transducer elements. The first ultrasound waves and the second ultrasound wave may be transmitted from different sub-regions of the transducer. Additionally or alternatively, the first ultrasound waves may be transmitted by the first sub-region and the reflections are measured by the second sub-region, the first sub-region being different from the second sub-region. In some embodiment, the first ultrasound waves are transmitted by the first sub-region of the transducer and the reflections are subsequently measured by the first sub-region.

In various embodiments, the method includes (e) transmitting the second ultrasound waves to the acoustic reflector and/or a second acoustic reflector based on the adjusted parameter value, and repeating steps (c), (d), and (e) until a stopping condition is satisfied. The stopping condition may include a phase difference between currently measured reflections and previously measured reflections being below a threshold and/or a number of iterations exceeding a predetermined limit. In some embodiments, the method includes (e) transmitting second ultrasound waves, based on the adjusted parameter value, to the target region to cause generation of one or more secondary acoustic reflectors therein, and repeating steps (b), (c), (d), and (e) until a stopping condition is satisfied. The stopping condition includes a phase difference between currently measured reflections and previously measured reflections being below a threshold and/or a number of iterations exceeding a predetermined limit.

In another aspect, the invention relates to a system for focusing an ultrasound transducer. In various embodiments, the system includes an ultrasound transducer having multiple transducer elements; and a controller configured to (a) cause generation of one or more acoustic reflectors in the target region using the ultrasound transducer; (b) transmit the first ultrasound waves to the target region; (c) measure reflections of the first ultrasound waves off the acoustic reflector; and (d) based at least in part on the measured reflections, adjust a parameter value associated with one or more transducer elements so as to improve an ultrasound focus at the target region. The parameter value may include a frequency, a phase, and/or an amplitude of a signal driving the transducer element(s) for generating the first ultrasound waves. In one implementation, the controller is further configured to initially estimate the parameter value based on a measurement of transmitted or reflected ultrasound waves. In addition, the system may include an administration device for introducing an ultrasound contrast agent into the target region. In one embodiment, the system includes a detector device for measuring the reflections off the acoustic reflector. In another embodiment, the system includes an imager and/or a detector device for detecting generation of the acoustic reflector.

The controller may be configured to cause the transducer elements to measure the reflections off the acoustic reflector. In addition, the controller may be configured to cause the first ultrasound waves to generate the acoustic reflector. In some embodiments, the controller is further configured to cause the transducer elements to transmit the second ultrasound waves to the target region so as to generate the acoustic reflector, the second ultrasound waves being transmitted to the target region prior to the first ultrasound waves. In one implementation, the second ultrasound waves have a value of a constitutive parameter different from that of the first ultrasound waves. The constitutive parameter may be, for example, an intensity level and/or a frequency associated with the ultrasound waves. In some embodiments, the controller is further configured to transmit the first ultrasound waves and/or the second ultrasound waves based at least in part on a physical model.

In various embodiments, the ultrasound transducer includes multiple sub-regions, each sub-region having multiple transducer elements. The controller is configured to cause different sub-regions of the transducer to transmit the first ultrasound waves and the second ultrasound waves. In one embodiment, the controller is further configured to cause the first sub-region to transmit the first ultrasound waves and the second sub-region to measure the reflections, the first sub-region being different from the second sub-region. Additionally or alternatively, the controller may be configured to cause the first sub-region of the transducer to transmit the first ultrasound waves and subsequently measure the reflections.

In various embodiments, the controller is further configured to (e) transmit the second ultrasound waves to the acoustic reflector and/or a second acoustic reflector based on the adjusted parameter value, and repeat steps (c), (d), (e) until a stopping condition is satisfied. The stopping condition may include a phase difference between currently measured reflections and previously measured reflections being below a threshold and/or a number of iterations exceeding a predetermined limit. In some embodiments, the controller is further configured to (e) transmit the second ultrasound waves, based on the adjusted parameter value, to the target region to cause generation of one or more secondary acoustic reflectors therein, and repeat steps (b), (c), (d), and (e) until a stopping condition is satisfied. The stopping condition includes a phase difference between currently measured reflections and previously measured reflections being below a threshold and/or a number of iterations exceeding a predetermined limit.

As used herein, the term "substantially" means±10%, and in some embodiments, ±5% of the peak intensity. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
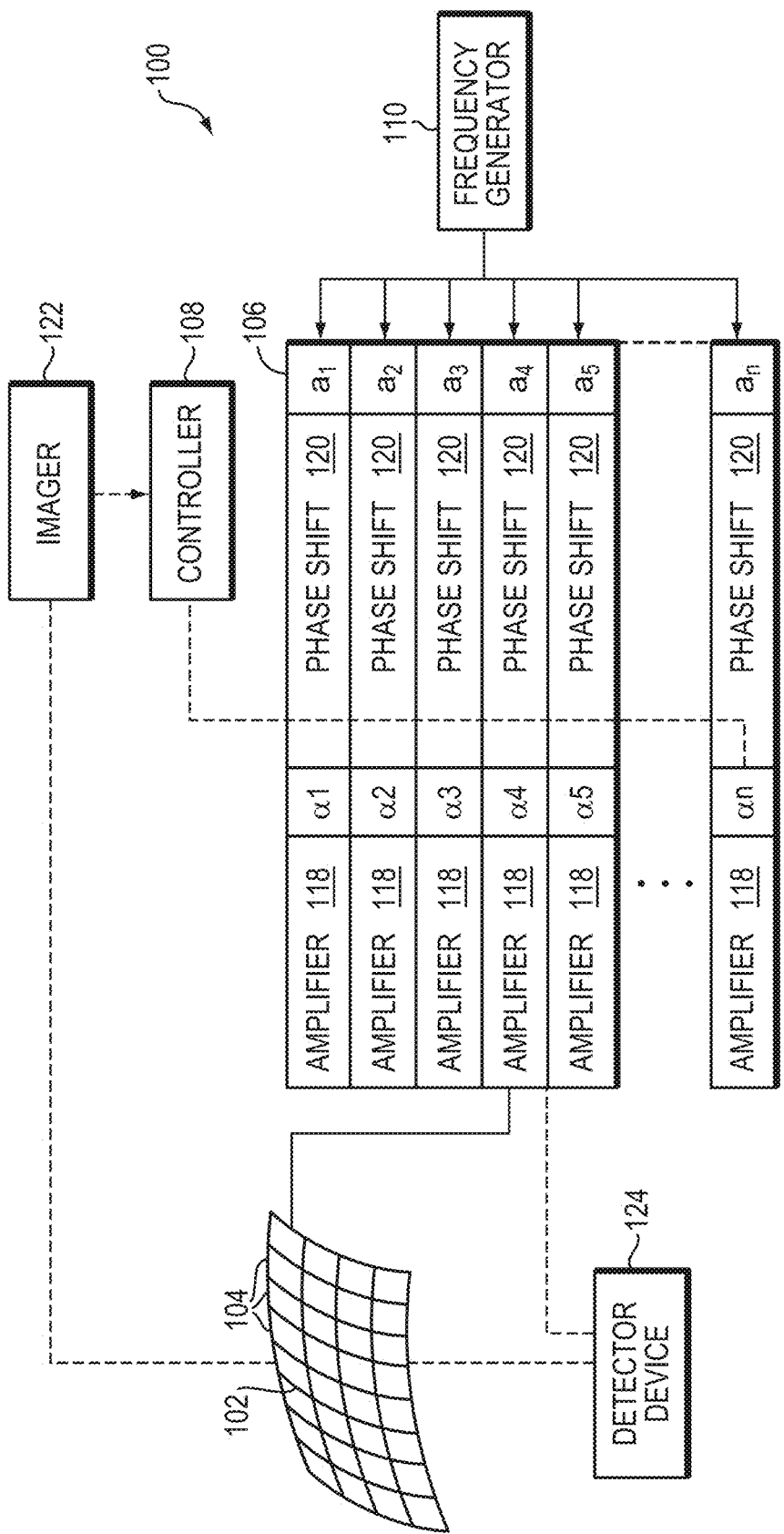
FIG. 1 illustrates a focused ultrasound system in accordance with various embodiments.

FIG. 1 illustrates an exemplary ultrasound system 100 for focusing ultrasound onto a patient's brain through the skull.

One of ordinary skill in the art, however, will understand that the ultrasound system 100 described herein may be applied to any part of the human body. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on the surface of the skull or a body part other than the skull, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase delay circuit 120; drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through inhomogeneous tissue (e.g., the patient's skull) onto the target region (e.g., a region in the patient's brain). Via adjustments of the amplification factors and/or the phase shifts, a desired shape and intensity of a focal zone may be created at the target region.

The amplification factors and phase shifts may be computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, to determine the frequency, phase shifts and/or amplification factors of the transducer elements 104. In certain embodiments, the controller computation is based on information about the characteristics (e.g., structure, thickness, density, etc.) of the skull and their effects on propagation of acoustic energy. In various embodiments, such information is obtained from an imager 122, such as a magnetic resonance imaging (MRI) device, a computer tomography (CT) device, a positron emission tomography (PET) device, a single-photon emission computed tomography (SPECT) device, or an ultrasonography device. The imager 122 may provide a set of two-dimensional images suitable for reconstructing a three-dimensional image of the skull from which thicknesses and densities can be inferred; alternatively, image acquisition may be three-dimensional. In addition, image-manipulation functionality may be implemented in the imager 122, in the controller 108, or in a separate device.

System 100 may be modified in various ways within the scope of the invention. For example, for diagnostic applications, the system may further include a detector device (e.g., a hydrophone) 124 that measures transmitted or reflected ultrasound, and which may provide the signals it receives to the controller 108 for further processing. The reflection and transmission signals may also provide an alternative or additional source for determination of the phase shifts and/or amplification factors or feedback for the phase and amplitude adjustments of the beamformer 106. The system 100 may contain a positioner for arranging the array 102 of transducer elements 104 with respect to the patient's skull. In order to apply ultrasound therapy to body parts other than the brain, the transducer array 102 may take a different (e.g., cylindrical) shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Figure 2:
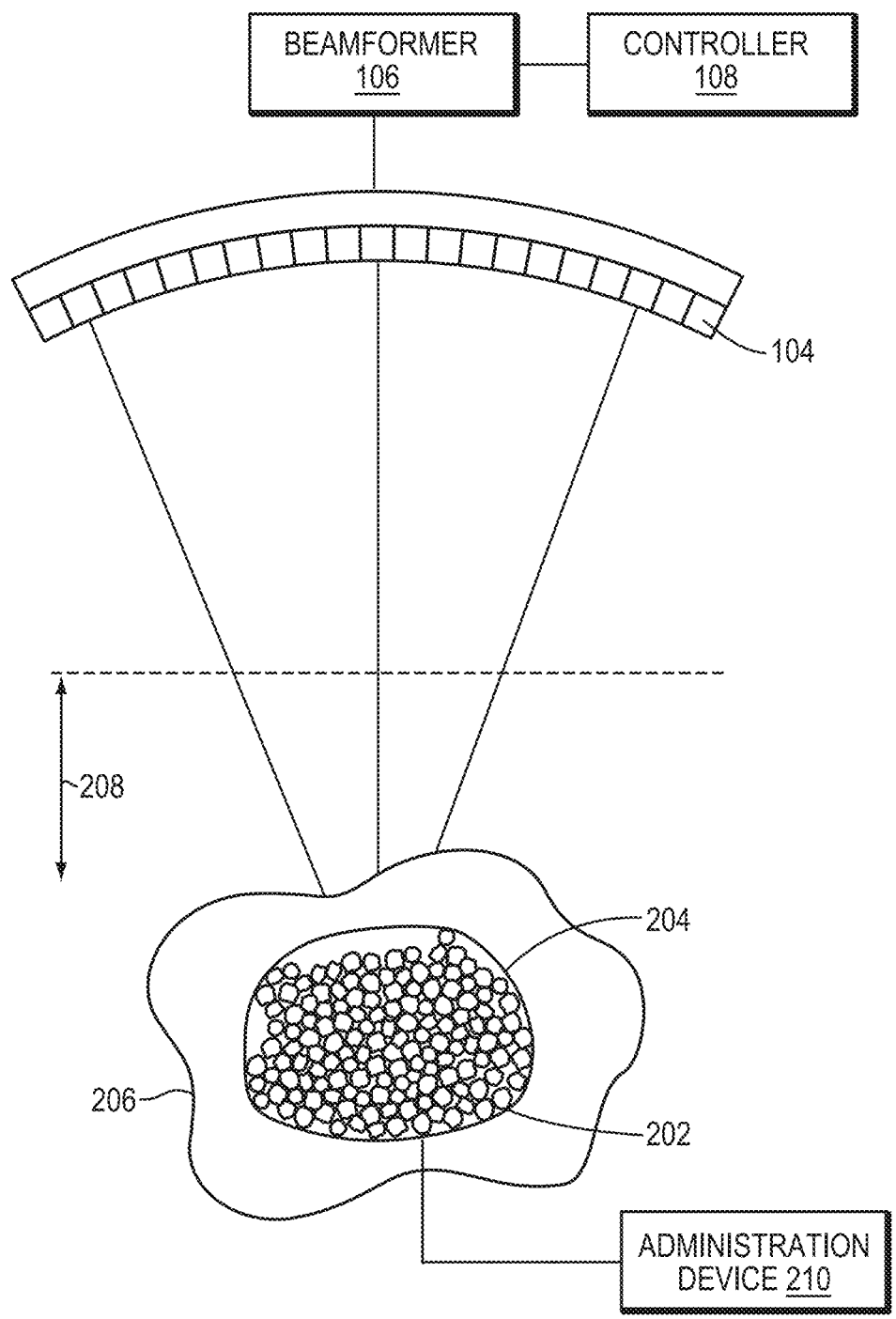
FIG. 2 depicts ultrasound beams delivered to a target tissue region and thereby causing generation of microbubbles in tissue located in a focal zone of the transducer in accordance with various embodiments.

Referring to FIG. 2, in various embodiments, the controller 108 causes the beamformer 106 to provide drive signals to the transducer elements 104 above an intensity threshold such that the acoustic energy emitted by the transducer elements 104 may generate a bubble or a small cloud of gas bubbles (or "microbubbles") 202 in the liquid contained in the tissue. The gas bubbles can be formed due to the negative pressure produced by the propagating ultrasonic waves or when the heated liquid ruptures and is filled with gas/vapor. In one embodiment, the controller 108 estimates the intensity and/or phase shift of the ultrasound wave emitted from each transducer element 104 using a physical model. For example, the physical model may predict focusing properties (e.g., the shape, size and location of the focus zone 204) based on information about the geometry of the transducer elements 104 and their locations and orientations relative to the target region 206 as well as the amplitudes and phases of ultrasound waves transmitted from the elements 104. In addition, the physical model may take into account transducer output errors resulting from, for example, transducer elements 104 moving or shifting from their expected location during manufacturing, use and repair and/or as a result of the elements 104 being deformed by heat. Additional information concerning the approach of determining the transducer output errors is provided in U.S. Pat. No. 7,535,794, the contents of which are incorporated herein by reference.

In some embodiments, the physical model further includes parameters, such as material properties (e.g., the energy absorption of the tissue or the speed of sound at the employed frequency) along the beam path for predicting the focusing properties. Again, the material properties may be collected using the imager 122 as described above and/or other suitable devices. By providing certain inputs, such as the desired focusing properties, the expected and actual geometries of the transducer elements 104 and their locations and orientations relative to the target region 206, the physical model can compute the required amplitudes and/or phases associated with the transducer elements 104 to produce a focus at the target region 206. In a simplified example, all transducer elements 104 transmit ultrasound waves having a single amplitude value but various phase shifts so as to create a focal intensity above the threshold of microbubble formation.

Alternatively, the intensity levels and/or relative phases of the transducer elements 104 may be determined based on transmitted and/or reflected ultrasound measured either prior to or during treatment (e.g., during treatment setup). In addition, these measurements may be utilized to adjust parameters of the physical prediction model. In any case, the estimated intensity levels and/or relative phases of the ultrasound beam may be sufficient to generate the microbubbles 202 in the focal zone 204 that is substantially close to the target region 206, yet without the need to account perfectly for acoustic aberrations caused by inhomogeneous intervening tissue.

Transmission of ultrasound energy at the intensity above the threshold level of microbubble generation may be relatively brief, e.g., occurring over a duration of several milliseconds or less, yet sufficiently long to generate microbubbles 202 within the focal zone 204 without substantially generating microbubbles in tissue outside the focal zone 204 (e.g., in the near field 208); this minimizes heating in the surrounding tissue. Further, although the threshold intensity may differ with each patient and/or tissue structure, appropriate threshold intensities may be readily determined by those skilled in the art, e.g., through the use of a monitoring mechanism sensitive to the generation of microbubbles 202. For example, the formation of microbubbles 202 may be monitored using the imager 122 and/or the ultrasound detector device 124.

In some embodiments, the microbubbles 202 are introduced into the patient's body intravenously using an administration device 210, and may either be injected systemically into the patient or locally into the target region. For example, microbubbles 202 may be introduced into the patient's body in the form of liquid droplets that subsequently vaporize, gas-filled bubbles, or other similar substances, such as conventional ultrasound contrast agents.

Because of their encapsulation of gas therein, the microbubbles 202 act as reflectors of ultrasound and the reflections therefrom can be used to obtain information about the focusing properties at the target region 206. Accordingly, in some embodiments, once the formation of the microbubbles 202 is detected (using, for example, images acquired by the imager 122 or reflected signals detected by the detector device 124), the controller 108 may re-energize the transducer elements 104 to transmit ultrasound waves to the generated microbubbles and start an auto-focusing procedure as further described below; the re-emitted ultrasound beams may have the same or different intensity levels and/or phase shifts as the beams utilized for creating the microbubbles 202.

Figure 3A:
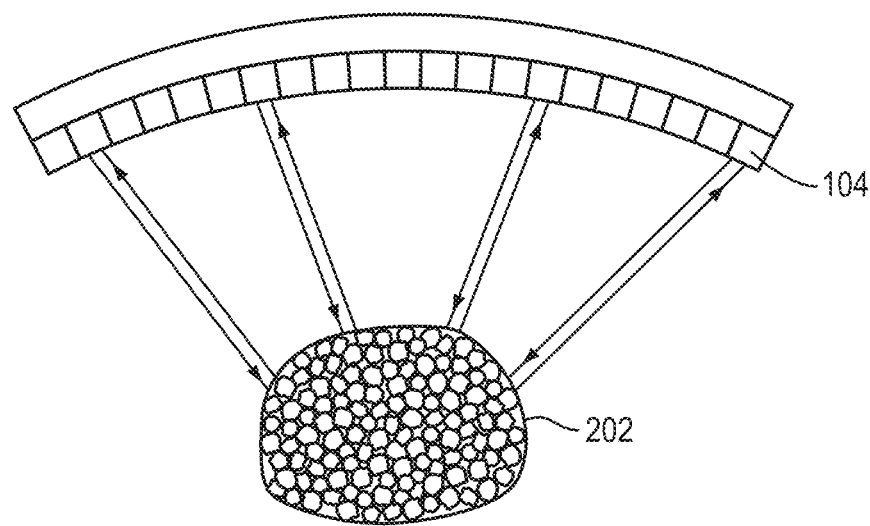
FIGS. 3A-3C depict various configurations of the transducer elements performing an auto-focusing method in accordance with various embodiments.
Figure 3B:
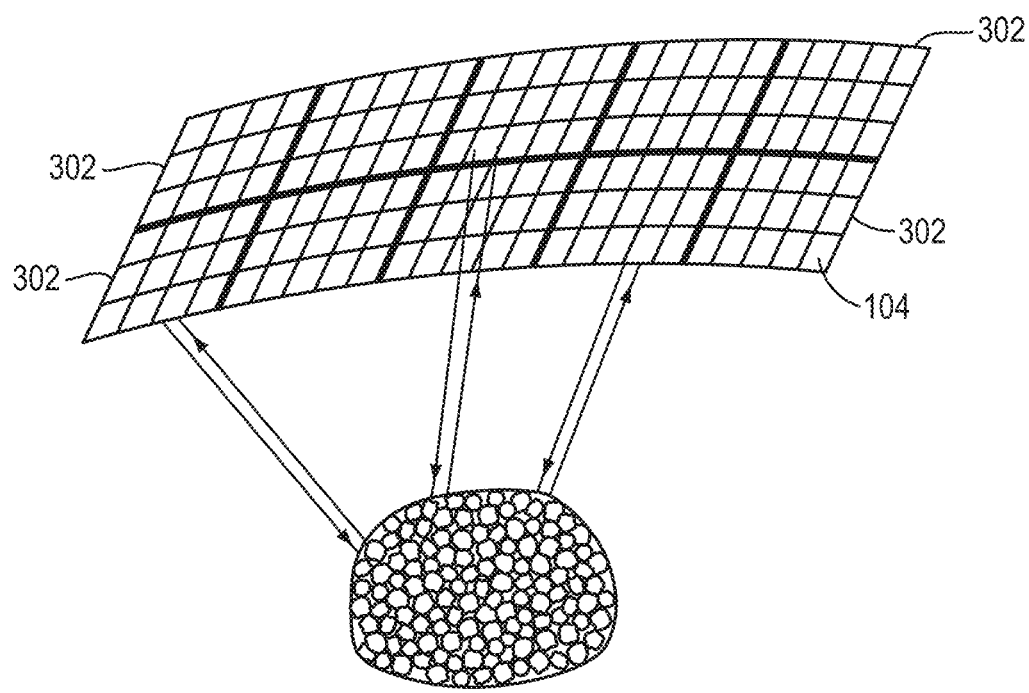
Figure 3C:
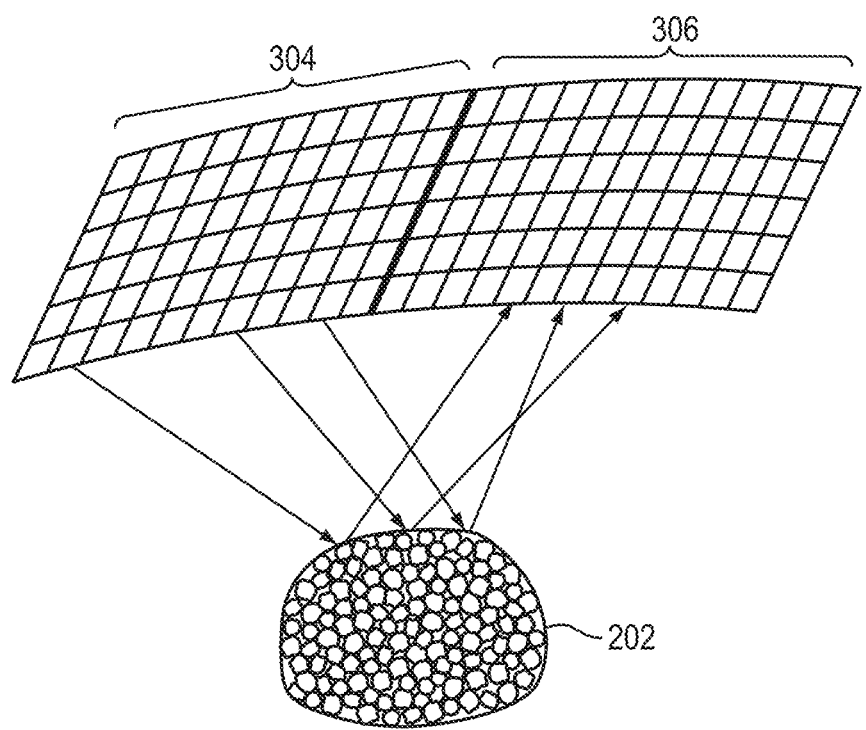

Ultrasound reflections from the microbubbles 202 may be measured using the detector device 124, which then transmits the resulting signals to the controller 108. Alternatively, the transducer elements 104 may possess both transmit and detect capabilities. Referring to FIG. 3A, in one embodiment, each individual transducer element 104 alternates between transmitting ultrasound signals to the microbubbles and receiving ultrasound signals reflected therefrom. For example, all transducer elements 104 may substantially simultaneously transmit ultrasound to the microbubbles 202 and subsequently receive echo signals therefrom. Referring to FIG. 3B, in one implementation, the transducer array is divided into multiple sub-regions 302; each sub-region 302 comprises a one- or two-dimensional array (i.e., a row or a matrix) of transducer elements 104. The sub-regions 302 may be separately controllable, i.e., they are each capable of (i) emitting ultrasound waves at amplitudes and/or phases that are independent of the amplitudes and/or phases of the other sub-regions 302, and (ii) measuring reflected waves off the microbubbles 202. In one embodiment, the sub-regions 302 are assigned different amplitudes and/or phases from one another, and activated, one at a time, to transmit ultrasound to and receive reflections from the microbubbles 202. Referring to FIG. 3C, in another embodiment, the transducer array is divided into a transmit region 304 and a receive region 306; transducer elements in the transmit region 304 transmit the ultrasound waves while transducer elements in the receive region 306 receive the reflected waves. The received reflected waves are then transmitted to the controller 108 for analysis. The transmit region 304 and receive region 306 of may be configured in different patterns and shapes at various locations of the transducer array.

Once the measured wave reflected signals are provided to the controller 108, the controller 108 may analyze them to obtain information, such as the amplitudes and/or phases, associated with the reflection beams. In one embodiment, the controller 108 compares the phases of the measured reflections, $\varphi_{ref}$, to the phases of the transmitted waves, $\varphi_{tra}$, determines the difference therebetween ($\Delta\varphi = \varphi_{ref} - \varphi_{tra}$), and operates the transducers elements 104 in accordance with the difference. For example, the controller 108 may cause each transducer element 104 to transmit another ultrasound beam having a phase shift of the determined phase difference, $\Delta\varphi$, to the focal point 204 and measure the resulting reflections from the microbubbles 202. Again, the phase difference between the reflected and transmitted ultrasound may be set as the phase value correction for the next sonication. This process can be iteratively implemented until the phase difference between the reflected and transmitted waves is below a threshold value (e.g., 10°), which indicates that the ultrasound beams focus at the target region with desired focusing properties (e.g., having a desired shape and/or an optimal power for thermal treatment). The phase shift adjusting procedure may be terminated when other conditions are met. For example, the phase shift adjustment may be stopped when too may iterations (e.g., more than 20 times) have been performed or when the improvement of the deviation between two successive iterations is too small (e.g., $\Delta\varphi_{n+1} - \Delta\varphi_n < 5°$).

The amplitudes of the ultrasound waves in each sonication during the focusing process may be the same or different. In one embodiment, after formation of the microbubbles, the intensity of the beams is lowered below the threshold level of microbubble collapsing and, maintained at the lower intensity during the next sonication(s) so as to generate a focal zone in the target region without collapsing the microbubbles 202. The resulting reflections are detected and measured to ensure that the focal zone has the desired properties. If not, the necessary adjustments are made based on the deviation between the reflected signals and what was expected. After the focusing process is complete, the first treatment ultrasound transmission may be delayed to allow the microbubbles 202 to at least partially dissipate and/or collapse. If ultrasound contrast agents are introduced for microbubble formation during the focusing process, treatment may be postponed until the generated microbubbles substantially collapse or at least until the enhanced ultrasound energy absorption that they cause are minimized.

In other embodiments, treatment is performed in the presence of microbubbles 202—i.e., the treatment ultrasound sonications are delivered in the presence of microbubbles 202. As the microbubbles 202 may oscillate at the frequency of the delivered ultrasound waves and/or generate some limited local cavitation, they may serve to increase the mechanical-to-thermal energy conversion, enhance absorption of the energy at the focal zone and thereby ablate the target tissue faster and more efficiently.

In various embodiments, the controller 108 includes all necessary hardware components and/or software modules to automatically perform certain functions as described above (e.g., analysis of the reflected signals, comparison of the measured phase to the transmitted phase, and/or adjustments of the phases/amplitudes). Accordingly, the focusing approach as described herein may be performed automatically. As an alternative, the analysis of the reflected signals and/or adjustments of the phases/amplitudes may be partially performed manually by a user to create a high-quality ultrasound focus.

Figure 4:
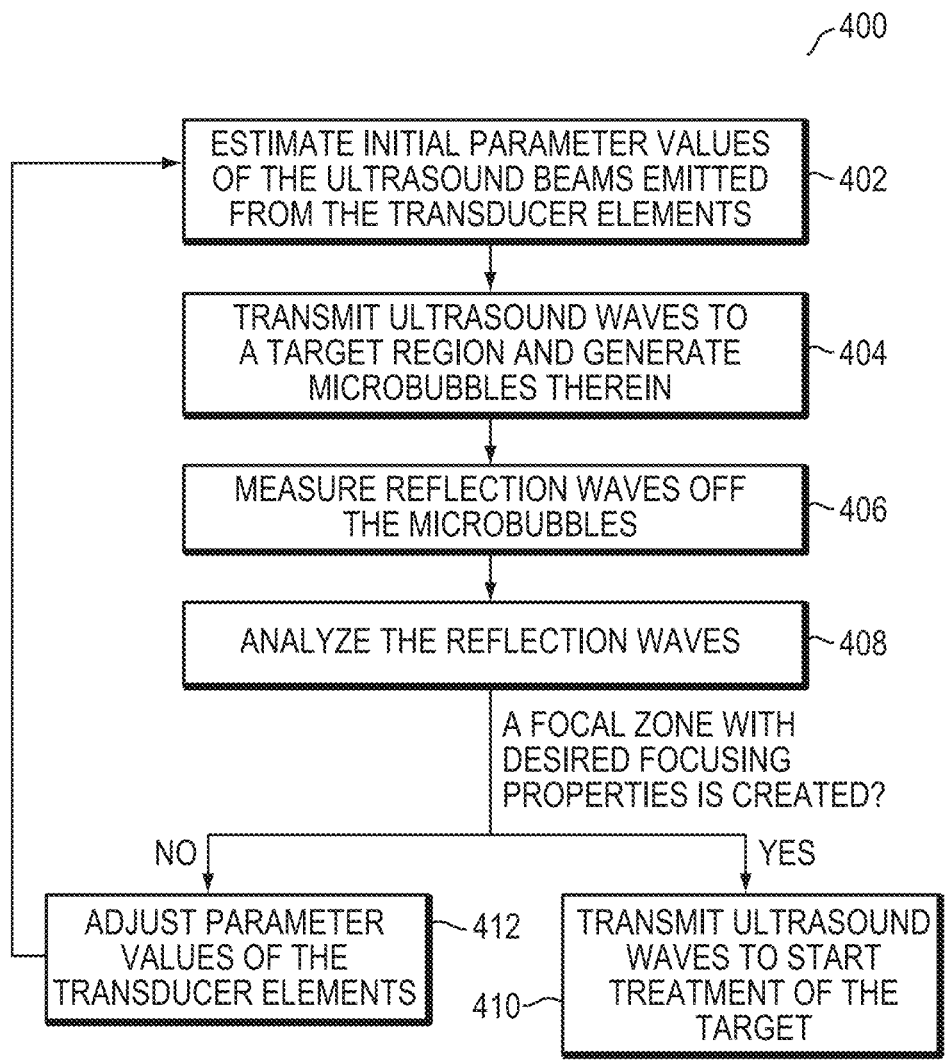
FIG. 4 is a flow chart illustrating an auto-focusing approach in accordance with various embodiments.

FIG. 4 is a flow chart 400 illustrating an ultrasound focusing approach in accordance with various embodiments. In a first step 402, initial parameter values (e.g., frequencies, amplitudes and/or phases) of the ultrasound beams emitted from the transducer elements are estimated using, for example, a physical model and/or measurements of the transmitted and/or reflected ultrasound. In a second step 404, based on the estimated parameter, the transducer elements transmit ultrasound waves to a target region and generate microbubbles therein. In a third step 406, ultrasound reflected from the microbubbles is measured. In a fourth step 408, the measured reflections are analyzed to determine whether a focal zone with desired focusing properties is created at the target region. If so, the transducer elements transmit ultrasound waves based on the current values of the transducer parameter to start treatment of the target (step 410). If not, a new set of parameter values of the transducer elements is determined based on the measured reflection waves, and the ultrasound elements apply the new set of values to direct waves to the microbubbles (step 412). Steps 406, 408, 412 are then repeated until desired focusing properties are achieved at the target region. In each iteration, the ultrasound waves may be transmitted to the same or different microbubbles from that in the previous iteration(s); as a result, the reflections received in two iterations may be from the same or different microbubbles. Accordingly, this approach allows the ultrasound beams to auto-focus at the target region despite the presence of inhomogeneous intervening tissue.

One of ordinary skill in the art will understand that variations in the focusing approach described above are possible and are thus within the scope of the present invention. For example, it may not be necessary to activate a majority of the transducer elements 104 for performing focusing using cavitation bubbles as described herein, and the number of transducer elements activated in each sonication may vary. For example, a fraction of the transducer elements 104 (e.g., every one out of ten elements) may be selected to transmit and/or receive ultrasound waves in a first sonication for creating microbubbles 202. The computed phase differences associated with the selected transducer elements may then be interpolated, extrapolated or processed using any suitable estimation approach to obtain the phase differences associated with unselected transducer elements. In the next sonication, a fraction of the previously unselected transducer elements may be used to repeat the focusing steps—i.e., transmitting ultrasound waves to the microbubbles 202 based on the interpolated (or extrapolated) phase differences and receiving reflections off the microbubbles 202. The selected transducer elements in the current sonication may or may not include the selected transducer elements in the precedent sonication(s) and the number of selected elements may be different in each sonication.

Further, the microbubbles 202 may be alternatively generated using a conventional dual-frequency approach—i.e., the ultrasound beams are delivered at one frequency to generate microbubbles 202 in the focal zone 204, and subsequently delivered at another frequency to start the auto-focusing approach as described above. One of skill in the art will understand that any variations utilizing microbubbles 202 for auto-focusing ultrasound beams at the target region 206 are within the scope of the present invention.

In general, functionality for performing auto-focusing of ultrasound beams, including, computing initial values of transducer parameters (e.g., frequencies, amplitudes and/or phases) associated with the transducer elements (based on a physical model and/or measurements), analyzing the reflected signals, determining new parameter values of the transducer elements and/or adjusting ultrasound operations, as described above, whether integrated within a controller of the imager, and/or an ultrasound system, or provided by a separate external controller, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A system for focusing an ultrasound transducer comprising:
   an ultrasound transducer comprising a plurality of transducer elements; and
   a controller configured to:
   (a) cause generation of one or more microbubbles in a target region using the ultrasound transducer;
   (b) transmit ultrasound waves, based on initial parameter values associated with the transducer elements, to the target region;
   (c) cause a detector device or a sub-region of the ultrasound transducer to measure reflections of the ultrasound waves transmitted in step (b) off at least one of the one or more microbubbles in the target region;
   (d) based at least in part on the measured reflections, adjust a parameter value associated with at least one of the transducer elements;
   (e) transmit ultrasound waves, based on the adjusted parameter value, to the target region;
   (f) cause the detector device or the sub-region of the ultrasound transducer to measure reflections of the ultrasound waves transmitted in step (e) off at least one of the one or more microbubbles in the target region; and
   (g) repeat steps (d), (e), and (f) until a stopping condition is satisfied,
   wherein the stopping condition corresponds to a deviation between (i) a phase difference between ultrasound waves transmitted in step (e) and measured reflections thereof and (ii) a phase difference between ultrasound waves transmitted in a previous iteration of step (e) and measured reflections thereof, being below a threshold.

2. The system of claim 1, wherein the controller is configured to cause the detector device to measure the reflections.

3. The system of claim 1, wherein the controller is further configured to cause an imager and/or the detector device to detect generation of the one or more microbubbles in the target region.

4. The system of claim 1, wherein the controller is configured to cause the sub-region of the ultrasound transducer to measure the reflections.

5. The system of claim 1, wherein the controller is further configured to cause the ultrasound waves transmitted in step (b) to generate the one or more microbubbles in the target region in step (a).

6. The system of claim 1, wherein the controller is further configured to, in step (a), cause the transducer elements to transmit ultrasound waves to the target region so as to generate the one or more microbubbles before transmission of the ultrasound waves in step (b).

7. The system of claim 6, wherein the controller is further configured to transmit the ultrasound waves transmitted in at least one of step (a) or step (b) based at least in part on a physical model.

8. The system of claim 6, wherein the controller is further configured to transmit the ultrasound waves in step (a) having a value of a constitutive parameter different from that of the ultrasound waves in step (b).

9. The system of claim 8, wherein the constitutive parameter comprises at least one of an intensity level or a frequency.

10. The system of claim 6, wherein the ultrasound transducer comprises a plurality of sub-regions, each sub-region comprising a plurality of transducer elements, wherein the plurality of sub-regions includes the sub-region in step (c).

11. The system of claim 10, wherein the controller is further configured to cause different sub-regions of the transducer to transmit ultrasound waves in different iterations of step (e).

12. The system of claim 10, wherein the controller is further configured to cause a first sub-region to transmit the ultrasound waves in step (e) and the sub-region to measure the reflections in step (f), the first sub-region being different from the sub-region.

13. The system of claim 10, wherein the controller is further configured to cause the sub-region of the transducer to transmit the ultrasound waves in step (e) and subsequently measure the reflections in step (f).

14. The system of claim 1, wherein the controller is further configured to initially estimate the parameter value based on a measurement of transmitted or reflected ultrasound waves.

15. The system of claim 1, wherein the parameter value comprises at least one of a frequency, a phase, or an amplitude of a signal driving at least one of the transducer elements.

* * * * *